(12) United States Patent
Abramoff et al.

(10) Patent No.: US 11,232,548 B2
(45) Date of Patent: Jan. 25, 2022

(54) SYSTEM AND METHODS FOR QUALIFYING MEDICAL IMAGES

(71) Applicant: Digital Diagnostics Inc., Coralville, IA (US)

(72) Inventors: Michael D. Abramoff, University Heights, IA (US); Ben Clark, Cedar Rapids, IA (US); Eric Talmage, Byron Center, MI (US); John Casko, Iowa City, IA (US); Warren Clarida, Cedar Rapids, IA (US); Meindert Niemeijer, Prairie Village, KS (US); Timothy Dinolfo, Coralville, IA (US); Tay Stutts, Iowa City, IA (US)

(73) Assignee: Digital Diagnostics Inc., Coralville, IA (US)

( * ) Notice: Subject to any disclaimer, the term of this patent is extended or adjusted under 35 U.S.C. 154(b) by 0 days.

(21) Appl. No.: 15/466,636

(22) Filed: Mar. 22, 2017

(65) Prior Publication Data
US 2017/0278241 A1    Sep. 28, 2017

Related U.S. Application Data

(60) Provisional application No. 62/311,660, filed on Mar. 22, 2016.

(51) Int. Cl.
*G06T 7/00* (2017.01)
*G16H 30/20* (2018.01)
*G16H 30/40* (2018.01)

(52) U.S. Cl.
CPC ............ *G06T 7/0002* (2013.01); *G16H 30/20* (2018.01); *G16H 30/40* (2018.01);
(Continued)

(58) Field of Classification Search
CPC .......... G06F 19/30; G06T 2207/10101; G06T 2207/30041; G06T 2207/30168; G06T 7/0002
See application file for complete search history.

(56) References Cited

U.S. PATENT DOCUMENTS 7,532,942 B2 *   5/2009   Reiner .................... G16H 15/00
                                                            700/90
10,013,639 B1 *  7/2018   Schurman ............. G06F 16/583
                  (Continued)

OTHER PUBLICATIONS

Fairbanks A, Myers (Provencher) L, Flanary W, Warner L, Boldt HC. Ocular Ultrasound: A Quick Reference Guide for the On-Call Physician. EyeRounds.org. posted Feb. 4, 2016; Available from: http://www.EyeRounds.org/tutorials/ultrasound/ (Year: 2016).*

*Primary Examiner* — Amandeep Saini
(74) *Attorney, Agent, or Firm* — Fenwick & West LLP

(57) ABSTRACT

Disclosed is a system for qualifying medical images submitted by user for diagnostic analysis comprising: an image input module, configured to receive one or more image input by a user; an image protocol conformation module, configured to receive the one or more images from the image input module, and further configured to analyze each of the one or more images for conformity with a predefined protocol and wherein images that do not conform to the predefined protocol are flagged as non-conforming images; an image output module, configured to identify to the user each of the one or more images flagged as non-conforming and prompting the user to resubmit a new image for each of the non-conforming images; and an image resubmission module, configured to receive the user resubmitted image and provide the resubmitted image to the image protocol conformation module.

14 Claims, 5 Drawing Sheets

(52) U.S. Cl.
CPC .............. *G06T 2207/10101* (2013.01); *G06T 2207/30041* (2013.01); *G06T 2207/30168* (2013.01)

(56) References Cited

U.S. PATENT DOCUMENTS

| | | | | |
|---|---|---|---|---|
| 2004/0221855 | A1* | 11/2004 | Ashton | G06F 19/345 128/898 |
| 2005/0157848 | A1* | 7/2005 | Miyauchi | A61B 6/56 378/207 |
| 2006/0119622 | A1* | 6/2006 | Kariathungal | G16H 40/63 345/653 |
| 2006/0238546 | A1* | 10/2006 | Handley | H04N 1/0045 345/619 |
| 2007/0237308 | A1* | 10/2007 | Reiner | G16H 40/20 378/207 |
| 2008/0044069 | A1* | 2/2008 | DuGal | G16H 30/20 382/128 |
| 2010/0021027 | A1* | 1/2010 | Hartkens | G16H 10/20 382/128 |
| 2010/0303363 | A1* | 12/2010 | Fedorovskaya | G06T 7/0002 382/199 |
| 2011/0054266 | A1* | 3/2011 | Dinino | A61B 8/00 600/300 |
| 2011/0188718 | A1* | 8/2011 | Hill | G16H 30/20 382/128 |
| 2011/0242306 | A1* | 10/2011 | Bressler | A61B 3/12 348/78 |
| 2013/0182220 | A1* | 7/2013 | Naba | A61B 3/14 351/206 |
| 2013/0322711 | A1* | 12/2013 | Schultz | A61B 5/445 382/128 |
| 2014/0029828 | A1* | 1/2014 | Schwartz | G06T 7/0012 382/131 |
| 2015/0029464 | A1* | 1/2015 | Jayasundera | G06T 7/254 351/246 |
| 2016/0155229 | A1* | 6/2016 | Shinoda | G16H 50/50 382/131 |

* cited by examiner

SYSTEM AND METHODS FOR QUALIFYING MEDICAL IMAGES

CROSS-REFERENCE TO RELATED APPLICATION(S)

This application claims priority to U.S. Provisional Application No. 62/311,660, filed Mar. 22, 2016, which is hereby incorporated by reference in its entirety under 35 U.S.C. § 119(e).

TECHNICAL FIELD

The disclosure relates to systems and methods for image-based medical diagnostics.

BACKGROUND

Medical imaging—and ophthalmic imaging, in particular—require a level of precision when it comes to capturing visual data about a patient and their state of health. Automated systems can be useful in determining whether a given set of medical images meet the requirement of a given protocol in terms of quality, field size, and field location. Conformity to these requirements is particularly important when utilizing automated screening tools, which require consistent formatting for downstream processing and diagnostic analysis. Thus, there is a need in the art for an automated system to determine whether user submitted images conform with image parameters required for further diagnostic processing and analysis.

BRIEF SUMMARY

Disclosed herein is system for qualifying medical images submitted by user for diagnostic analysis comprising: an image input module, configured to receive one or more image input by a user; an image protocol conformation module, configured to receive the one or more images from the image input module, and further configured to analyze each of the one or more images for conformity with a predefined protocol and wherein images that do not conform to the predefined protocol are flagged as non-conforming images; an image output module, configured to identify to the user each of the one or more images flagged as non-conforming and prompting the user to resubmit a new image for each of the non-conforming images; and an image resubmission module, configured to receive the user resubmitted image and provide the resubmitted image to the image protocol conformation module.

In certain aspects, the predefined protocol is comprised of one or more image parameters and wherein protocol conformation is established when the image conforms with each of the one or more parameters. In further aspects, the one or more image is an ocular image. In still further aspects, the ocular image is a retinal image. In yet further aspects, the retinal image is a fundus camera image or an optical coherence tomography (OCT) image.

In certain aspects, the one or more image parameters are image quality, field size, and/or retinal coverage. According to certain further aspects, the one or more image parameters further comprise foveal location within the image field and/or optic disk location within the image field. In still further aspects, the output module is further configured to guide the user in selecting or generating an image that corrects the non-conformity of the non-conforming image.

According to certain further aspects, the system is configured to provide for iterative improvement of image conformity. In further aspects, the image protocol conformation module is configured to analyze conformity of each of the one or more images with the predefined protocol by way of an algorithm. In further aspects, the algorithm is modified by machine learning from example protocols. In still further aspects, the algorithm is a rule based algorithm. According to still further aspects, the system further comprises a graphic user interface. In yet further aspects, the image protocol conformation module is housed in a server.

DETAILED DESCRIPTION

Figure 1:
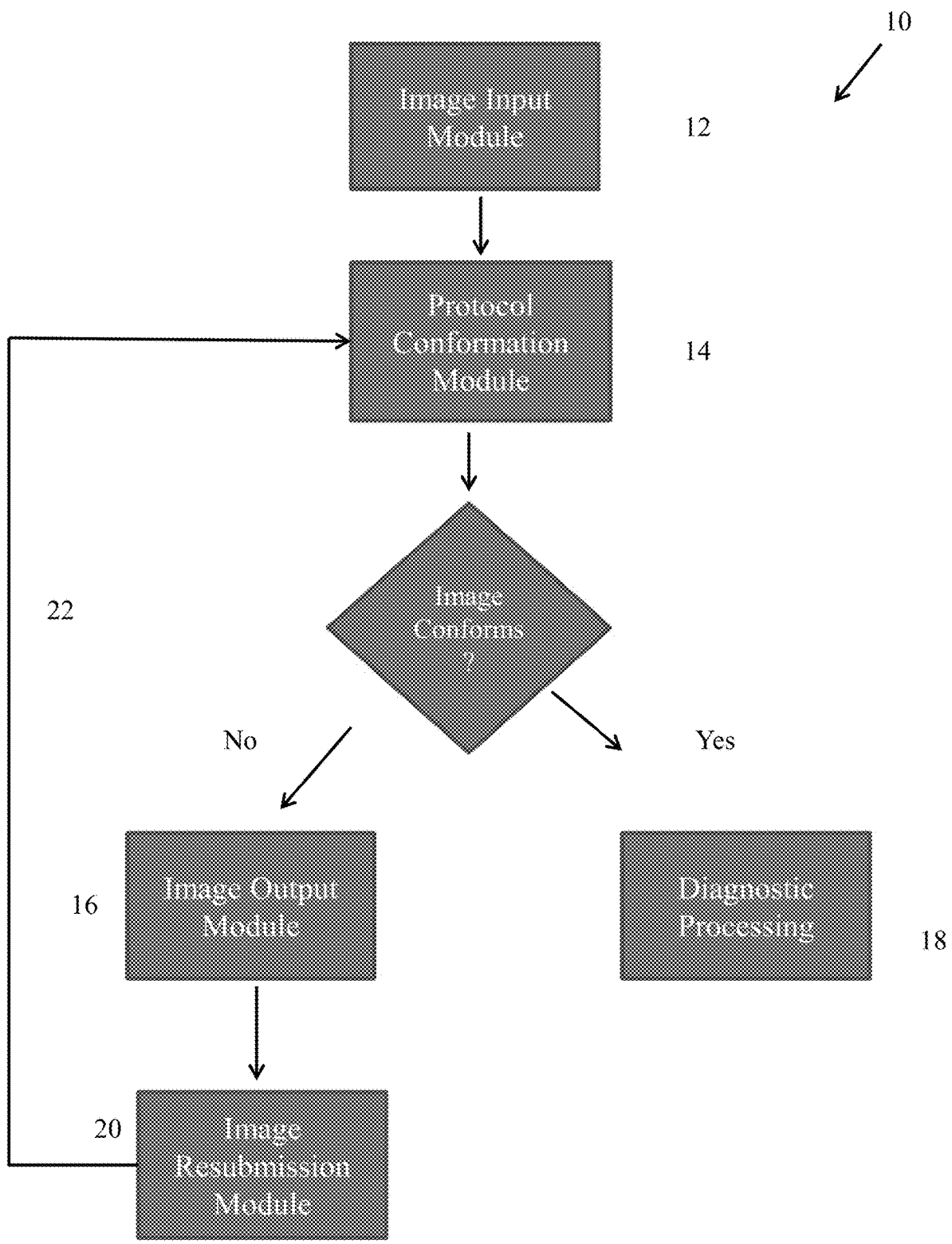
FIG. 1 is a flowchart representation of the disclosed system, according to certain embodiments.

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. One general aspect includes an image input module, configured to receive one or more image input by a user. The system also includes an image protocol conformation module, configured to receive the one or more images from the image input module, and further configured to analyze each of the one or more images for conformity with a predefined protocol and where images that do not conform to the predefined protocol are flagged as non-conforming images. The system also includes an image output module, configured to identify to the user each of the one or more images flagged as non-conforming and prompting the user to resubmit a new image for each of the non-conforming images. The system also includes an image resubmission module, configured to receive the user resubmitted image and provide the resubmitted image to the image protocol conformation module. Other embodiments of this aspect include corresponding computer systems, apparatus, and computer programs recorded on one or more computer storage devices, each configured to perform the actions of the methods.

Implementations may include one or more of the following features. In certain embodiments, the image protocol conformation module is comprised of one or more image parameters and protocol conformation is established when the image conforms with each of the one or more parameters. Such parameters may include, but are not limited to image quality, field size, and the portion of the tissue being imaged included in the image.

In certain embodiments, the one or more image is an ocular image, for example, a retinal image. One skilled in the art will appreciate that other ocular regions are possible. Retinal images may be acquired through a number of methods know in the art, including but not limited to use of a fundus camera or through optical coherence tomography (OCT). In these embodiments, the one or more image parameters may be image quality, field size, and/or retinal coverage. Further parameters in these embodiments include foveal location within the image field and/or optic disk location within the image field.

According to certain embodiments, the output module is further configured to guide the user in selecting or generating an image that corrects the non-conformity of the non-conforming image. In certain implementations of these embodiments, the system is configured to provide for iterative improvement of image conformity through successive rounds of user resubmission, with each round bringing the image closer into conformity.

According to certain implementations, the image protocol conformation module is configured to analyze conformity of each of the one or more images with the predefined protocol by way of an algorithm. In certain embodiments, the algorithm is modified by machine learning from example protocols. In further embodiments, the algorithm is a rule based algorithm.

In certain embodiments, the system includes a graphic user interface to facilitate user image input and provide feedback to the user with respect to non-conforming images. Implementations of the described techniques may include hardware, a method or process, or computer software on a computer-accessible medium. In certain embodiments, the image protocol conformation module is housed in a server. In further embodiments, the server is a cloud-based server.

Turning now to the figures, FIG. 1 shows a flowchart of the system according to certain embodiments. In these embodiments, the user inputs images into the image input module 12 which provides the images to the protocol conformation module 14. The protocol conformation module 14 analyzes the images for conformation with the predefined protocol parameters. For images that conform with the protocol parameters, the images are ready for further diagnostic processing 18. Images that do not conform are sent to the image output module 16 along with information for the user to determine the manner in which the image is non-conforming. The user then selects or generates a new image to correct the non-conforming attribute(s) of the non-conforming image and inputs the new image into the image resubmission module 20. The image resubmission module 20 then directs 22 the resubmitted image to the protocol conformation module 14 to analyze whether the resubmitted image conforms. This process can be repeated iteratively until a conforming image is supplied.

Figure 2:
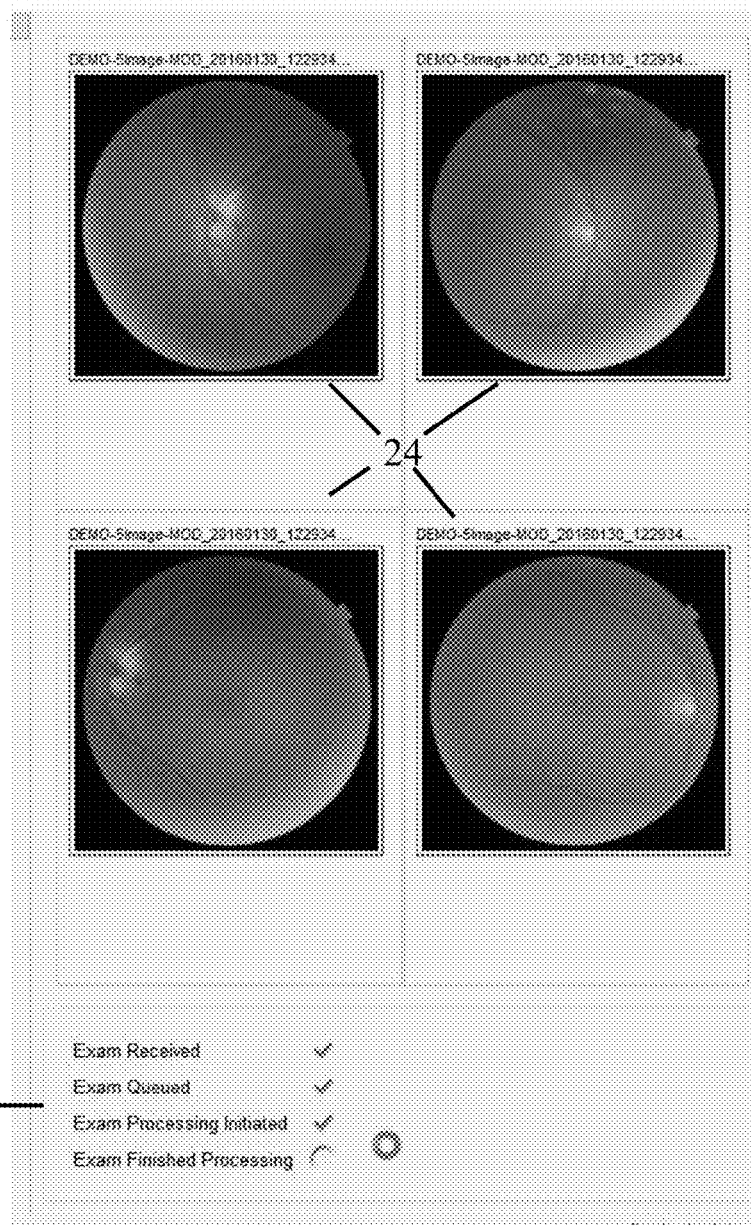
FIG. 2 shows a screen shot of a graphic user interface of the system, according to certain embodiments.
Figure 3:
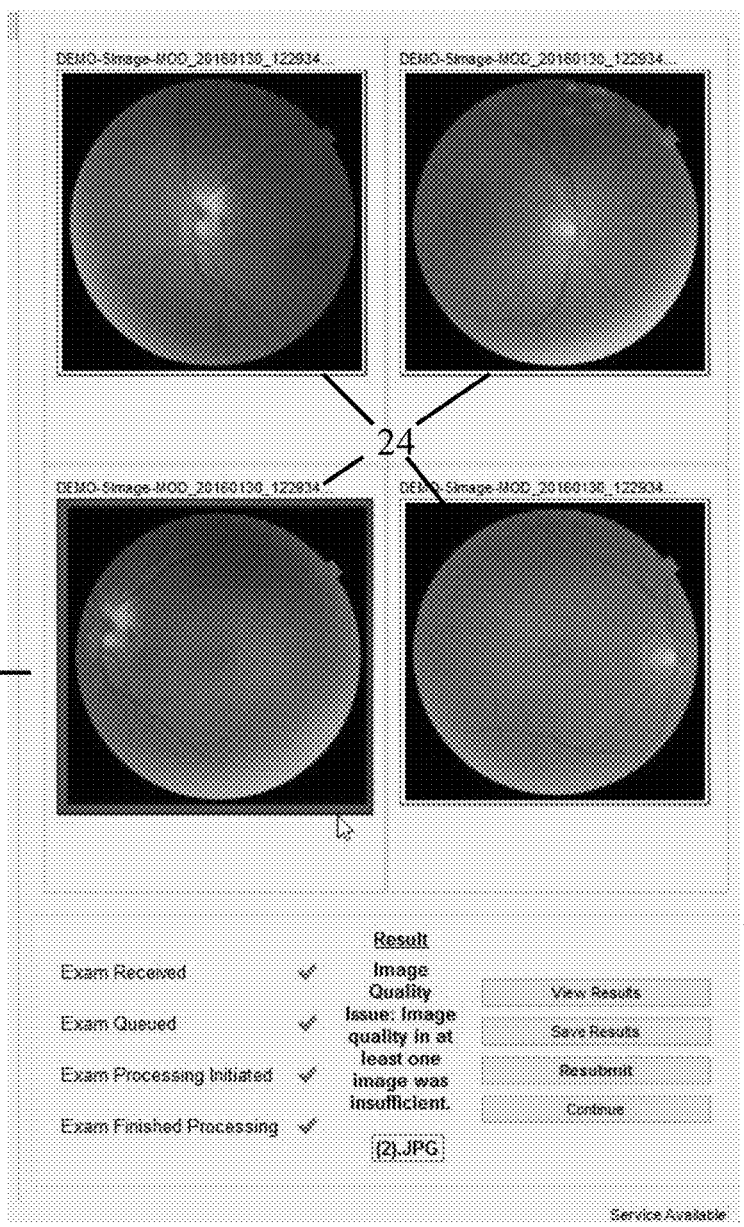
FIG. 3 shows a screen shot of a graphic user interface of the system, according to certain embodiments.
Figure 4:
FIG. 4 shows a screen shot of a graphic user interface of the system, according to certain embodiments.
Figure 5:
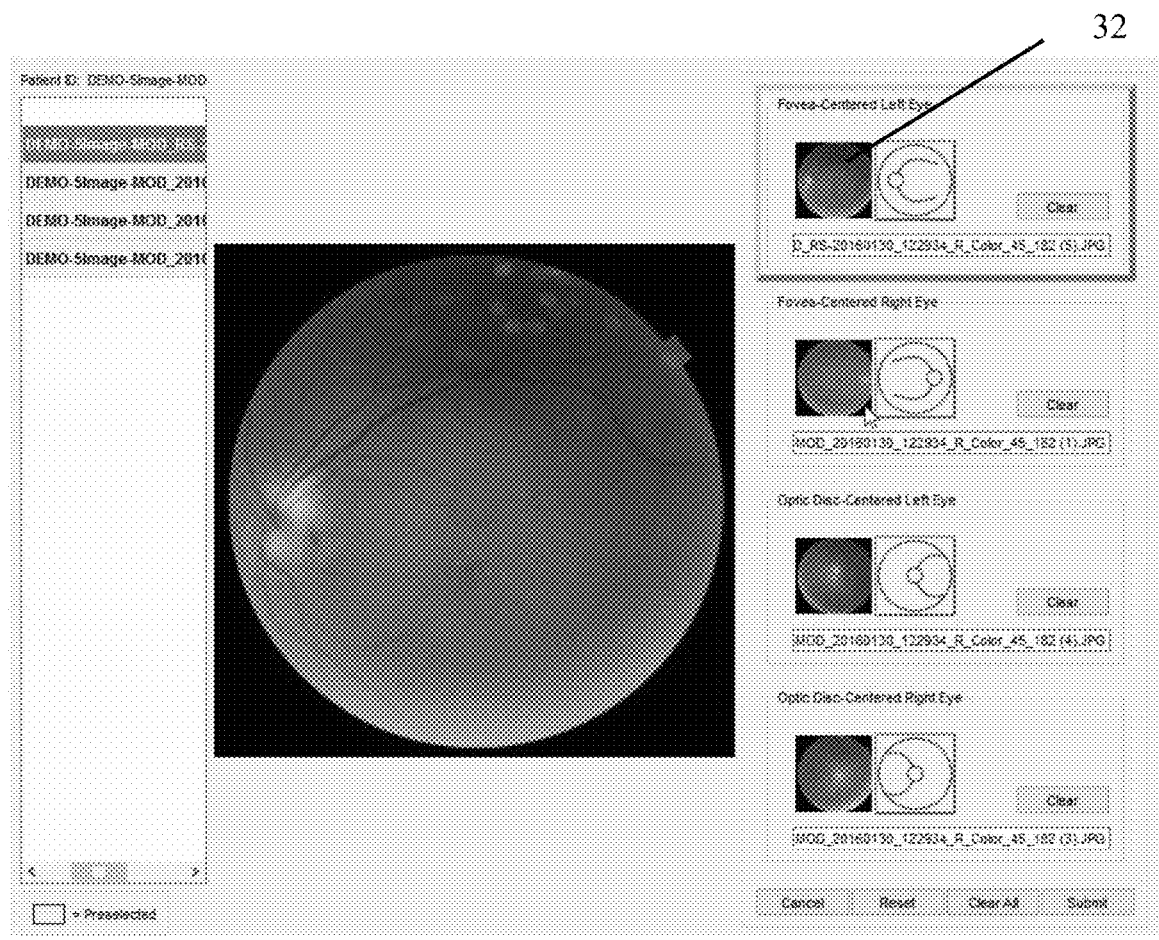
FIG. 5 shows a screen shot of a graphic user interface of the system, according to certain embodiments.

FIGS. 2-5 show screen shots of the graphic user interface (GUI), according to certain embodiments. FIG. 2 shows a screen shot of the GUI for the user input module and shows that the user has input four retinal images 24 for analysis. A system progress display 26 shows the user the progress of the system in analyzing image conformity. FIG. 3 shows the GUI of the image output module indicating that one of the images 28 has been flagged as non-conforming. FIG. 4 shows a screenshot of the GUI of the image resubmission module. The resubmission module indicates to the user that the fovea centered left eye image is non-conforming 30. FIG. 5 shows the user input of a new conforming image 32 into the resubmission module.

Although the disclosure has been described with reference to preferred embodiments, persons skilled in the art will recognize that changes may be made in form and detail without departing from the spirit and scope of the disclosed apparatus, systems and methods.

What is claimed is:

1. A system for qualifying medical images submitted by a user for diagnostic analysis comprising:
    a non-transitory computer-readable medium comprising memory with instructions encoded thereon; and
    one or more processors configured to, when executing the instructions, perform operations comprising:
        receiving a plurality of retinal images input by a user, each of the plurality of retinal images capturing a different portion of a retina, wherein the different portions of a retina captured in the plurality of retinal images comprise an optic disk and a fovea, each different portion of a retina corresponding to a respective predefined protocol, wherein the respective protocol corresponding to the optic disk comprises having the optic disk at a center of a field of the respective retinal image, and wherein the respective protocol corresponding to the fovea comprises having the fovea at a center of a field of the respective retinal image;
        analyzing each respective one of the plurality of retinal images for conformity with the respective predefined protocol corresponding to the captured portion of the retina in the respective retinal image, and flagging a retinal image that does not conform to its respective predefined protocol as a non-conforming image, the retinal image flagged based on either the optic disk not being at a center of a field of a respective retinal image or the fovea not being at a center of a field of a respective retinal image;
        generating for display a graphical interface to the user, the graphical interface comprising each of the plurality of retinal images that were not flagged as non-conforming, and excluding the non-conforming image, wherein the graphical interface includes a placeholder cell for resubmitting a new image of the portion of the retina captured by the non-conforming image;
        receiving the user resubmitted image; and
        replacing the placeholder cell with the resubmitted image responsive to determining that the resubmitted image conforms to the respective predefined protocol corresponding to the captured portion of the retina.

2. The system of claim 1, wherein each respective predefined protocol is comprised of one or more image parameters and wherein protocol conformation is established when its respective retinal image conforms with each of the one or more parameters.

3. The system of claim 1, wherein each retinal image is at least one of a fundus camera image or an optical coherence tomography (OCT) image.

4. The system of claim 3, wherein each respective protocol comprises one or more retinal image parameters including image quality, field size, and/or retinal coverage.

5. The system of claim 1, wherein the operations further comprise guiding the user in selecting or generating the user resubmitted image that corrects the non-conformity of the non-conforming image.

6. The system of claim 5, wherein the system is configured to perform the guiding iteratively through multiple candidate replacement images.

7. The system of claim 1, wherein analyzing each respective one of the plurality of retinal images for conformity with its respective predefined protocol comprises implementing machine learning from example protocols.

8. The system of claim 1, wherein analyzing each respective one of the plurality of retinal images for conformity with its respective predefined protocol comprises utilizing rule based heuristics.

9. The system of claim 1, further comprising a graphic user interface.

10. The system of claim 1, wherein the one or more processors are at least partially housed in a server.

11. A method for qualifying medical images submitted by a user for diagnostic analysis, the method comprising:
receiving a plurality of retinal images input by a user, each of the plurality of retinal images capturing a different portion of a retina, wherein the different portions of a retina captured in the plurality of retinal images comprise an optic disk and a fovea, each different portion of a retina corresponding to a respective predefined protocol, wherein the respective protocol corresponding to the optic disk comprises having the optic disk at a center of a field of the respective retinal image, and wherein the respective protocol corresponding to the fovea comprises having the fovea at a center of a field of the respective retinal image;
analyzing each respective one of the plurality of retinal images for conformity with the respective predefined protocol corresponding to the captured portion of the retina in the respective retinal image, and flagging a retinal image that does not conform to its respective predefined protocol as a non-conforming image, the retinal image flagged based on either the optic disk not being at a center of a field of a respective retinal image or the fovea not being at a center of a field of a respective retinal image;
generating for display a graphical interface to the user, the graphical interface comprising each of the plurality of retinal images that were not flagged as non-conforming, and excluding the non-conforming image, wherein the graphical interface includes a placeholder cell for resubmitting a new image of the portion of the retina captured by the non-conforming image;
receiving the user resubmitted image; and
replacing the placeholder cell with the resubmitted image responsive to determining that the resubmitted image conforms to the respective predefined protocol corresponding to the captured portion of the retina.

12. The method of claim 11, wherein each respective predefined protocol is comprised of one or more image parameters and wherein protocol conformation is established when its respective retinal image conforms with each of the one or more parameters.

13. The method of claim 11, wherein each retinal image is at least one of a fundus camera image or an optical coherence tomography (OCT) image.

14. A non-transitory computer-readable medium comprising memory with instructions encoded thereon for qualifying medical images submitted by a user for diagnostic analysis, the instructions causing one or more processors to perform operations when executed, the instructions comprising instructions to:
receive a plurality of retinal images input by a user, each of the plurality of retinal images capturing a different portion of a retina, wherein the different portions of a retina captured in the plurality of retinal images comprise an optic disk and a fovea, each different portion of a retina corresponding to a respective predefined protocol, wherein the respective protocol corresponding to the optic disk comprises having the optic disk at a center of a field of the respective retinal image, and wherein the respective protocol corresponding to the fovea comprises having the fovea at a center of a field of the respective retinal image;
analyze each respective one of the plurality of retinal images for conformity with the respective predefined protocol corresponding to the captured portion of the retina in the respective retinal image, and flagging a retinal image that does not conform to its respective predefined protocol as a non-conforming image, the retinal image flagged based on either the optic disk not being at a center of a field of a respective retinal image or the fovea not being at a center of a field of a respective retinal image;
generate for display a graphical interface to the user, the graphical interface comprising each of the plurality of retinal images that were not flagged as non-conforming, and excluding the non-conforming image, wherein the graphical interface includes a placeholder cell for resubmitting a new image of the portion of the retina captured by the non-conforming image;
receive the user resubmitted image; and
replace the placeholder cell with the resubmitted image responsive to determining that the resubmitted image conforms to the respective predefined protocol corresponding to the captured portion of the retina.

* * * * *